US00PP23722P3

(12) United States Plant Patent
Cain et al.

(10) Patent No.: US PP23,722 P3
(45) Date of Patent: Jul. 9, 2013

(54) PLUM TREE NAMED 'SUPLUMFORTYFOUR'

(50) Latin Name: *Prunus salicina*
Varietal Denomination: Suplumfortyfour

(75) Inventors: David W. Cain, Bakersfield, CA (US); Terry A. Bacon, Bakersfiled, CA (US)

(73) Assignee: Sun World International, LLC, Bakersfield, CA (US)

( * ) Notice: Subject to any disclaimer, the term of this patent is extended or adjusted under 35 U.S.C. 154(b) by 67 days.

(21) Appl. No.: 13/373,321

(22) Filed: Nov. 10, 2011

(65) Prior Publication Data

US 2013/0125272 P1 May 16, 2013

(51) Int. Cl.
*A01H 5/00* (2006.01)

(52) U.S. Cl.
USPC ..... Plt./184

(58) Field of Classification Search
USPC ..... Plt./184
See application file for complete search history.

*Primary Examiner* — Annette Para
(74) *Attorney, Agent, or Firm* — Knobbe, Martens, Olson & Bear, LLP

(57) ABSTRACT

A new and distinct plum tree variety, *Prunus salicina*, cv. 'Suplumfortyfour' is characterized by large fruit with yellow skin.

1 Drawing Sheet

Latin name of the genus and species claimed: *Prunus salicina.*

Variety denomination: 'Suplumfortyfour'.

BACKGROUND AND SUMMARY OF THE INVENTION

This invention relates to the discovery and asexual propagation of a new and distinct variety of plum, *Prunus salicina* cv. 'Suplumfortyfour'. The new variety was first hybridized in March 1999 by David W. Cain and selected in June 2002 by Terry Bacon as breeder number: 'PL151YY'. The new variety was first evaluated by Terry Bacon near Wasco, Calif. in Kern County. The variety 'Suplumfortytfour' was originated by hybridization.

The new variety 'Suplumfortyfour' is characterized by large fruit with yellow skin.

The seed parent is '91P-045' (unpatented), and the pollen parent is '92P-033' (unpatented). The parent varieties were first crossed in March of 1999, with the date of sowing being January 2000, and the date of first flowering being March 2002. The new plum variety 'Suplumfortyfour' was first asexually propagated by Terry Bacon near Wasco, Kern County, Calif. in January 2003, by budding.

The new variety 'Suplumfortyfour' is distinguished from its seed parent, '91P-045' (unpatented), in that the new variety ripens about 7 days earlier than '91P-045' and has yellow skin compared to red skin for '91P-045'.

The new variety 'Suplumfortyfour' is distinguished from its pollen parent, '92P-033' (unpatented), in that the new variety ripens about 4 weeks earlier than '92P-033' and has yellow skin compared to black skin for '92P-033'.

The new variety 'Suplumfortyfour' has a similar ripening time as 'Black Amber' (unpatented), but has yellow skin compared to black skin for 'Black Amber.'

The new variety 'Suplumfortyfour' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new plum variety 'Suplumfortyfour'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to an 8 year old 'Suplumfortyfour' plants on Nemared (unpatented) rootstock, grown in the vicinity of Wasco, Kern County, Calif., during 2010, and is believed to apply to plants of the variety grown under similar conditions of soil and climate elsewhere.

TREE

General: (Measurements taken on 8 year old tree unless otherwise noted.)

*Size.*—Medium. Normal for most plum varieties. Reaches a height of approximately 3 meters with normal pruning.

*Spread.*—Approximately 3-5 meters.

*Vigor.*—Moderately vigorous, about 1.5 to 2 meters in height the first growing season.

*Growth.*—Semi-upright.

*Productivity.*—Productive, thinning and spacing of fruit is necessary.

*Form.*—Vase formed.

*Bearer.*—Regular.

*Fertility*.—Unknown, should be planted with another variety to ensure consistent production.
*Canopy density*.—Medium.
*Hardiness*.—Hardy in all fruit growing areas of California. Winter chilling requirement is approximately 600 hours at or below 7.2 C.
*Disease resistance/susceptibility*.—Under close observation in Kern County, Calif., no particular plant/fruit disease resistance/susceptibility has been observed.
*Insect resistance/susceptibility*.—Under close observation in Kern County, Calif., no particular plant/fruit insect resistance/susceptibility has been observed.

Trunk: (Measurements at approximately 30 cm above soil line on mature tree).
*Diameter*.—Approximately 20 cm, varies with soil type, fertility, climatic conditions and cultural practices.
*Texture*.—Medium shaggy, increases with age of tree.
*Trunk color*.—About Medium Grey-Brown 199B to Brown 200B; becomes darker with age.

Branches: (Measurements at approximately 90 cm above soil line.)
*Size*.—Diameter approximately 9 to 10 cm.
*Texture*.—Smooth on first year wood and increasing roughness with tree age.
*Color*.—Varying from about Medium Grey-Brown 199B to Brown 200B.
*Lenticels*.—Present.

Lenticels:
*Number*.—Numerous.
*Density*.—About 2/cm$^2$ but varies with tree vigor and climatic conditions.
*Color*.—About Medium Grey-Brown 199B.
*Size*.—Medium.
*Length*.—3 mm.
*Width*.—2 mm.

Flowering shoots: (Data taken in July at mid-point of current season growth.).
*Size*.—Average diameter approximately 5 mm.
*Color*.—Topside: About Medium Yellow-Green 152A. Underside: About Medium Yellow-Green 152A.
*Internode length*.—Medium; approximately 2 cm. Midway on flowering shoot.
*Flowering shoot lenticels*.—Medium amount. Color: About Medium Grey-Brown 199B. Diameter: Approximately 1.0 mm.
*Flowering shoot leaf buds*.—Shape: Obovate. Width: Approximately 1.5 mm. Length: Approximately 2.1 mm. Color: About Dark Greyed-Orange 177A.
*Flowering shoot flower buds*.—Shape: Elliptic. Width: Approximately 1 mm. Length: Approximately 1.8 mm. Color: About Dark Greyed-Orange 177A. Number of buds per node: Usually 2.
*Density of buds*.—Medium.
*Flower bud distribution*.—On spurs and one year old shoots.
*Ratio of wood (leaf) buds to flowering buds*.—½ on nodes.
*Anthocyanin intensity*.—None or very slight.

FOLIAGE

Leaves: (Data taken in July on fully expanded leaves at mid-point of the current season growth).
*Size*.—Medium.
*Average length*.—Medium; approximately 70 mm.
*Average width*.—Medium; approximately 35 mm.
*Thickness*.—Medium.
*Color*.—Upper surface: About Dark Green 131A. Lower surface: About Medium Green 137D.
*Form*.—Broad obovate.
*Tip*.—Cuspidate.
*Base*.—Irregularly V-shaped.
*Margin*.—Crenate.
*Venation*.—Pinately net veined.
*Vein color*.—About Medium Yellow-Green 146D on lower surface.
*Surface texture*.—Smooth.
*Leaf blade (ratio of length to width)*.—2:1.
*Shape in the cross section*.—Flat.
*Angle at apex*.—Small.
*Profile*.—Flat to slightly up folded.
*Leaf blade tip*.—Slightly curved downwardly.
*Angle of tip*.—Narrow.
*Undulation of margin*.—Medium.

Petiole:
*Average length*.—Medium; approximately 14 mm.
*Average diameter*.—Approximately 1.5 mm.
*Color*.—About Medium Yellow-Green 146D or darker with more light exposure.

Stipules:
*Number/leaf bud*.—Approximately 1 per leaf bud when present.
*Typical length*.—Approximately 3 mm.
*Color*.—About Medium Greyed-Orange 164B.
*Persistence*.—Falls off.

Leaf glands:
*Form*.—Globose.
*Average number*.—0-3, usually 2.
*Position*.—On petiole/leaf base transition area, alternate.
*Average size*.—Small; approximately 0.5 mm.
*Color*.—About Dark Grey-Brown 199A.

FLOWERS

General:
*Flower blooming period*.—First bloom: Approximately Feb. 25, 2010. Full bloom: Approximately Mar. 1, 2010.
*Location of first bloom*.—Older wood.
*Location of full bloom*.—Uniform throughout the canopy.
*Time of bloom*.—Medium.
*Duration of bloom*.—Medium; approximately 12 days.
*Diameter of fully opened flower*.—Medium, approximately 10 mm.
*Flower aroma*.—Very slight aroma.
*Shape*.—Rosaceous.

Peduncle:
*Length*.—Medium; approximately 10 mm.
*Diameter*.—Medium; approximately 1 mm.
*Color*.—About Medium Yellow-Green 144B.
*Pubescence*.—Absent.

Petals:
*Number*.—5.
*Arrangement*.—Overlapping slightly.
*Length*.—Approximately 12 mm.
*Diameter*.—Approximately 10 mm.
*Shape*.—Obovate.

*Apex shape*.—Rounded.
*Base shape*.—Narrows at point of attachment.
*Color of inner and outer surface*.—White.
*Surface texture*.—Smooth.
*Margins*.—Slightly undulating.
*Frequency of flowers with double petals*.—None.
*Size*.—Medium.
*Claw length*.—Medium.
*Margin waviness*.—Medium.
*Base angle*.—Narrow.
*Division of upper margin*.—Entire.
*Pubescence of inner surface*.—Absent.
*Pubescence of outer surface*.—Absent.

Sepals:
*Number*.—5.
*Length*.—Approximately 3 mm.
*Diameter*.—Approximately 2 mm.
*Shape*.—Elliptic.
*Color*.—About Medium Yellow-Green 144A.
*Surface texture*.—Smooth.
*Margins*.—Entire.
*Positioning*.—Adpressed to petals.
*Pubescence of inner surface*.—Absent.
*Pubescence of outer surface*.—Absent.
*Frequency of flowers with double sepals*.—None.

Stamens:
*Number*.—Ranges from about 20 to about 30, average 28.
*Average length*.—About 6 mm.
*Filament color*.—White.
*Anther color*.—About Medium Greyed-Orange 167A after starting to dry.
*Flower pollen color*.—About Light Greyed-Orange 163C when first opened.
*Position*.—Perigynous.

Pistil:
*Number*.—Usually one.
*Average length*.—Approximately 9 mm.
*Ovary diameter*.—Approximately 0.5 mm.
*Pubescence*.—None.
*Stigma extension in comparison to anthers*.—Level or slightly above anthers.
*Style frequency of supplementary pistils*.—Absent.

Flower buds:
*Hardiness*.—Hardy.
*Size*.—Medium.
*Length*.—Medium.
*Shape*.—Pointed.
*Positioning*.—Slightly free.
*Pubescence*.—Absent.
*Color*.—About Dark Greyed-Orange 177A.

Receptacle:
*Depth*.—Medium.
*Pubescence of inner surface*.—Absent.
*Pubescence of outer surface*.—Absent.

FRUIT

General: (Description taken near Wasco, Kern County, Calif. on Jun. 23, 2010).
*Date of first pick*.—Approximately Jun. 20, 2010.
*Date of last pick*.—Approximately Jun. 23, 2010.
*Maturity when described*.—Firm.
*Season ripening*.—Medium-early.
*Position of maximum diameter*.—Towards the middle.
*Symmetry about the suture*.—Symmetric.

Size:
*Length* (*stem end to apex*).—Approximately 65 mm.
*Diameter in line with suture plane*.—Approximately 65 mm.
*Diameter perpendicular to suture plane*.—Approximately 68 mm.
*Average weight*.—Approximately 153 gm.

Form:
*Viewed from apex*.—Rounded, symmetrical.
*Viewed from side, facing suture*.—Rounded, slightly flattened, symmetrical.
*Viewed from side, perpendicular to suture*.—Nearly round.

Apex shape: Flat to elongated.

Fruit stem cavity:
*Shape*.—Flaring.
*Depth*.—Medium; Approximately 8 mm.
*Breadth*.—Approximately 8 mm.
*Width*.—Narrow.

Fruit stem:
*Length*.—Medium; approximately 8 mm.
*Diameter*.—Approximately 2 mm.
*Color*.—About Medium Green 143C.
*Adherence to stone*.—Medium.

Fruit skin:
*Thickness*.—Medium.
*Adherence to flesh*.—Medium.
*Surface texture*.—Medium.
*Pubescence*.—None.
*Bloom*.—Slight.
*Ground color*.—About Light Yellow-Green 154A.
*Overcolor*.—About Light Yellow-Green 154C covering 99% f the fruit skin (yellow plum with no distinct overcolor/ground color regions, it is a blending of the two).
*Taste*.—Mildly Tart.
*Reticulation*.—Absent.
*Roughness*.—Absent.
*Tenacity*.—Tenacious to flesh.
*Tendency to crack*.—Slight.

Flesh:
*Ripens*.—Evenly.
*Texture*.—Fine-juicy.
*Fibers*.—Medium.
*Flavor*.—Bland-sweet.
*Brix*.—Approximately 15°.
*Juice*.—Abundant to moderate.
*Aroma*.—Slight.
*Color*.—Ranging from Medium Yellow 5D to Light Yellow 5A.
*Anthocyanin color under skin*.—Absent.
*Anthocyanin color of flesh*.—Absent.
*Anthocyanin color around stone*.—Absent.
*Amygdalin*.—Wanting
*Acidity*.—Low.
*Eating quality*.—Good.
*Stone/flesh ratio*.—1/30.
*Firmness*.—Medium.

Pit cavity size:
*Length*.—Approximately 20 mm.
*Diameter perpendicular to suture plane*.—Approximately 9 mm.
*Diameter in line with suture*.—Approximately 20 mm.

Fruit use: Fresh market.

Fruit shipping and keeping quality: Medium.

Stone:

*Stone freeness*.—Semi-free.

*Degree of adherence to flesh*.—Weak.

*Stone size*.—Size: Medium. Size compared to Fruit: Small. Length: Medium, approximately 20 mm. Diameter in line with suture plan: Approximately 20 mm. Diameter perpendicular to suture plane: Approximately 9 mm. Width of Stalk End: Medium. Angle of Stalk end: Acute angle. Hilum: Oval.

*Stone form*.—Viewed from side: Nearly oval with flattened base. Viewed from ventral end: Flattened, symmetrical. Viewed from Stem end: Flattened.

*Stone shape*.—Base shape: Nearly straight. Apex shape: Narrowing toward the apex with blunt end.

*Stone surface*.—Somewhat smooth with sharp ridges running from base to apex.

*Stone halves*.—Nearly symmetrical.

*Stone ridges*.—Mixture of continuous and non-continuous.

*Stone outgrowing keel*.—Partly-developed.

*Stone tendency to split*.—Slight in wet season.

*Stone color*.—About Light Greyed-Orange 164C when dried.

*Position of maximum*.—Middle.

*Sides*.—Nearly equal.

*Pits*.—Angular.

*Fibers*.—Parts from flesh smoothly.

*Ventrical edge*.—Medium.

*Dorsal edge*.—Narrow.

*Ground color*.—Not visible.

*Extent of overcolor*.—Medium.

*Pattern of overcolor*.—None.

Suture:

*Line*.—Shallow.

Ventral surfaces:

*Lips*.—Nearly equal.

*Depression of apex*.—Indistinct.

*Pistil base*.—Not persisting.

*Pubescence at apex*.—Absent.

Pistil point:

*Shape*.—Flattened to elongated.

What is claimed is:

1. A new and distinct plum tree as herein described and illustrated.

* * * * *

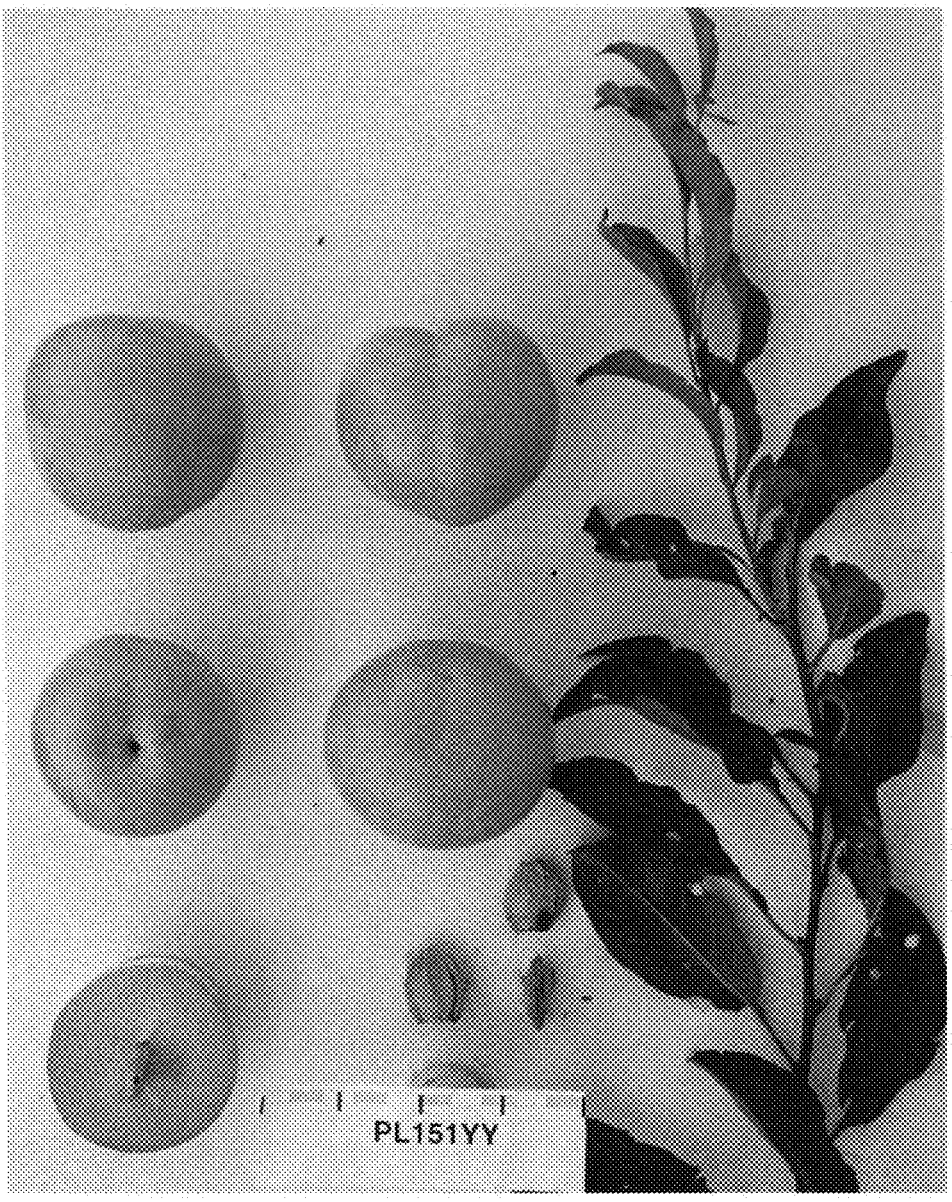
PL151YY